(12) United States Patent
Baugh et al.

(10) Patent No.: US 8,815,992 B2
(45) Date of Patent: Aug. 26, 2014

(54) TETRACARBOXYLIC ESTER PLASTICIZERS

(75) Inventors: Lisa Saunders Baugh, Ringoes, NJ (US); Enock Berluche, Phillipsburg, NJ (US); Karla Schall Colle, Magnolia, TX (US); Manika Varma-Nair, Warren, NJ (US); Ramzi Yanni Saleh, Baton Rouge, LA (US); Jon Edmond Randolph Stanat, Houston, TX (US); Stephen Zushma, Clinton, NJ (US); Victor DeFlorio, Cranford, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 10 days.

(21) Appl. No.: 13/085,905

(22) Filed: Apr. 13, 2011

(65) Prior Publication Data

US 2011/0257317 A1   Oct. 20, 2011

Related U.S. Application Data

(60) Provisional application No. 61/342,441, filed on Apr. 14, 2010.

(51) Int. Cl.
| | |
|---|---|
| *A61L 15/62* | (2006.01) |
| *C08K 5/12* | (2006.01) |
| *C07C 69/34* | (2006.01) |
| *C07C 69/74* | (2006.01) |
| *C08K 5/11* | (2006.01) |

(52) U.S. Cl.
CPC .  *C07C 69/34* (2013.01); *C08K 5/12* (2013.01); *C07C 2101/08* (2013.01); *C07C 69/74* (2013.01); *C08K 5/11* (2013.01)
USPC ........... 524/311; 524/306; 524/315; 560/233; 560/98

(58) Field of Classification Search
None
See application file for complete search history.

(56) References Cited

U.S. PATENT DOCUMENTS

| | | | |
|---|---|---|---|
| 3,211,691 | A | 10/1965 | Petropoulos et al. |
| 3,346,598 | A | 10/1967 | Van Volkenburgh et al. |
| 3,388,187 | A | 6/1968 | Sly et al. |
| 6,355,711 | B1 | 3/2002 | Godwin et al. |
| 6,740,254 | B2 | 5/2004 | Zhou et al. |
| 7,297,738 | B2 | 11/2007 | Gosse et al. |
| 2006/0247461 | A1 | 11/2006 | Schlosberg et al. |
| 2008/0242895 | A1 | 10/2008 | Godwin et al. |

FOREIGN PATENT DOCUMENTS

| | | | |
|---|---|---|---|
| EP | 09153287.9 | * | 2/2009 |
| JP | 71033933 B | | 7/1968 |
| JP | 53101311 | | 9/1978 |
| JP | 57170948 A | | 10/1982 |
| JP | 59-022950 | * | 2/1984 |
| JP | 59022950 | | 2/1984 |
| JP | 59118741 | | 7/1984 |
| JP | 1993098106 | | 4/1993 |
| JP | 06263915 A | | 9/1994 |
| JP | 8295649 | | 11/1996 |
| WO | 9932427 | | 7/1999 |
| WO | 03029339 | | 4/2003 |
| WO | 2004046078 | | 6/2004 |
| WO | WO 2010/079018 A1 | * | 7/2010 |

OTHER PUBLICATIONS

Full Translation of JP 59-022950 in English.*
U.S. Appl. No. 61/040,480.
U.S. Appl. No. 61/203,626.
A. D. Godwin, "Plasticizers" Applied Polymer Science 21st Century, edited by C. D. Craver and C. E. Carraher, Elsevier (2000), pp. 157-175.

* cited by examiner

*Primary Examiner* — Susannah Chung
*Assistant Examiner* — Robert T Butcher
(74) *Attorney, Agent, or Firm* — Robert A. Migliorini

(57) ABSTRACT

Tetraesters of a $C_4$-$C_5$ aliphatic tetracarboxylic acid and OXO-alcohols and plasticized compositions containing said tetraesters are provided.

14 Claims, 2 Drawing Sheets

TETRACARBOXYLIC ESTER PLASTICIZERS

CROSS-REFERENCE TO RELATED APPLICATIONS

This application claims priority to Provisional Application No. 61/342,441 filed on Apr. 14, 2010, and incorporated by reference herein in its entirety.

FIELD

This disclosure is related to a potential route to non-phthalate, OXO-tetraester plasticizers.

BACKGROUND

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for about 85% worldwide of PVC plasticizer usage in 2002. However, in the recent past there has been an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. For these and most other uses of plasticized polymer systems, however, a successful substitute for phthalate esters has heretofore not materialized.

One such suggested substitute for phthalates are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, WO 2004/046078, U.S. Application No. 2006-0247461, and U.S. Pat. No. 7,297,738.

Other suggested substitutes include esters based on benzoic acid (see, for instance, U.S. Pat. No. 6,740,254, and also co-pending, commonly-assigned, U.S. Provisional Patent Application No. 61/040,480, filed Mar. 28, 2008) and polyketones, such as described in U.S. Pat. No. 6,777,514; and also co-pending, commonly-assigned, U.S. patent application Ser. No. 12/058,397, filed Mar. 28, 2008. Epoxidized soybean oil, which has much longer alkyl groups ($C_{16}$ to $C_{18}$) has been tried as a plasticizer, but is generally used as a PVC stabilizer. Stabilizers are used in much lower concentrations than plasticizers. Copending and commonly assigned U.S. Provisional Patent Application No. 61/203,626, filed Dec. 24, 2008, discloses triglycerides with a total carbon number of the triester groups between 20 and 25, produced by esterification of glycerol with a combination of acids derived from the hydroformylation and subsequent oxidation of $C_3$ to $C_9$ olefins, having excellent compatibility with a wide variety of resins and that can be made with a high throughput.

U.S. Pat. No. 3,211,691, which is incorporated by reference herein in its entirety, discloses plasticized compositions comprising polymers of vinyl chloride and a tetraalkyl ester of cyclopentane 1,2,3,4-tetracarboxylic acid, wherein each of the alkyl groups contains from 3 to 12 carbon atoms, which can be derived from monohydric aliphatic alcohols including propyl alcohols, butyl alcohols, amyl alcohols, hexyl alcohols, heptyl alcohols, octyl alcohols, nonyl alcohols, decyl alcohols, undecyl alcohols, dodecyl alcohols and the like. The alkyl esters are not limited to homoalkyl esters but encompass mixed alkyl esters where one saturated aliphatic monohydric alcohol is used to esterify at least one but not more than three of the carboxyl groups in the cyclopentanetetracarboxylic acid while a different saturated aliphatic monohydric alcohol is utilized to esterify the remaining carboxyl groups.

U.S. Pat. No. 3,388,187 discloses derivatives of 1,2,3,4-cyclopentanetetracarboxylic acid having at least one unsaturated aliphatic ester moiety, suitable for cross-linking U.S. Pat. No. 3,346,598, which is incorporated by reference herein in its entirety, discloses novel esters, including tetra-esters of 1,2,3,4-cyclopentanetetracarboxylic acid useful as plasticizing agents. The alcohols used to prepare the esters contain four or more carbon atoms, and are preferably non-branched.

U.S. Pat. No. 6,355,711, which is incorporated by reference herein in its entirety, discloses a plasticizer ester prepared from the catalytic reaction of (1) at least one branched $C_7$-$C_{11}$ OXO-alcohol prepared from $C_6$-$C_{10}$ olefins with least 50% methyl branching at the beta carbon via hydroformylation, and (2) at least one acid or anhydride. Mono- and polybasic acids are disclosed.

JP 71033933 B discloses tetraesters of butane tetracarboxylic acid wherein the ester groups are $C_4$-$C_{18}$ alkyl or $C_7$-$C_{18}$ aralkyl, which are useful as plasticizers. JP 06263915 A discloses plasticizer compositions containing a 1,2,3,4-butane tetracarboxylate wherein the ester groups are $C_4$-$C_{36}$ alkyl or alkenyl groups, such as tetraoctyl-butane tetracarboxylate, and an additional ester compound. JP 57170948 A discloses vinyl chloride resins containing 20-200 phr tetraalkyl cyclopentanetetracarboxylates, such as tetrakis(2-ethylhexyl)cyclopentanetetra-carboxylate. JP 5098106 A discloses tetraesters of butanetetracarboxylic acid as plasticizers for PVC, wherein at least one of the ester groups is cyclohexyl. JP 59022950 discloses tetraesters of butanetetracarboxylic acid having $C_4$-$C_{10}$ alkyl sidechains as plasticizers for PVC, such as n-hexyl, n-octyl, and a mixture of n-hexyl and n-octyl. PVC compositions containing the tetraesters have improved cold and evaporation resistance. JP 59118741 discloses cyclopentane-tetracarboxylic ester plasticizers, having alkyl residues of mixed carbon numbers.

To date, none of the prior art compounds or compositions has demonstrated satisfactory equivalence to conventional phthalate plasticizers for use with PVC polymers. Thus what is needed is a method of making a general purpose non-phthalate plasticizer having suitable melting or chemical and thermal stability, pour point, glass transition, increased compatibility, good performance and low temperature properties.

SUMMARY

In a first embodiment, the present disclosure is directed to tetraesters of a $C_4$-$C_5$ aliphatic tetracarboxylic acid, such as 1,2,3,4-butanetetracarboxylic acid or 1,2,3,4-cyclopentane-tetracarboxylic acid, and OXO-alcohols.

In a preferred embodiment, the ester moieties are mixed-isomer alkyl residues of $C_5$ to $C_8$ OXO-alcohols, advantageously mixed-isomer alkyl residues of $C_5$ OXO-alcohols, or $C_6$ OXO-alcohols, or $C_7$ OXO-alcohols, or $C_8$ OXO-alcohols, including wherein the alkyl residues comprise a mixture of linear and branched alkyl groups.

Advantageously, the alkyl residues have from 0.05 to 0.4 beta branches per residue.

In another embodiment, the present disclosure is directed to a plasticizer compound of the formula:

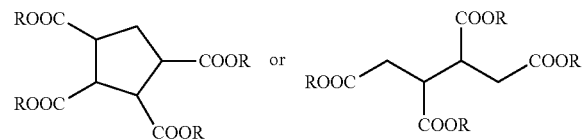

wherein each R is the alkyl residue of $C_5$ to $C_8$ OXO-alcohols, such as wherein collectively R represents mixed-isomer alkyl residues of $C_5$ to $C_8$ OXO-alcohols, preferably wherein each R is the alkyl residue of $C_5$ to $C_7$ OXO-alcohols, and more preferably wherein collectively R represents mixed-isomer alkyl residues of $C_5$ OXO-alcohols, or $C_6$ OXO-alcohols, or $C_7$ OXO-alcohols, or $C_8$ OXO-alcohols, including wherein the alkyl residues comprise a mixture of linear and branched alkyl groups.

Advantageously, the alkyl residues have from 0.05 to 0.4 beta branches per residue.

In a further embodiment, the disclosure is directed to a composition comprising a polymer and a plasticizer of the formula:

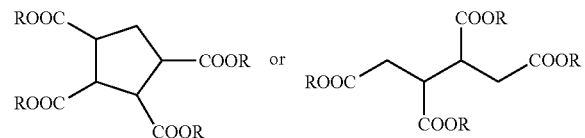

wherein each R is the alkyl residue of $C_5$ to $C_8$ OXO-alcohols, such as wherein collectively R represents mixed-isomer alkyl residues of $C_5$ to $C_8$ OXO-alcohols, preferably wherein each R is the alkyl residue of $C_5$ to $C_7$ OXO-alcohols, and more preferably wherein collectively R represents mixed-isomer alkyl residues of $C_5$ OXO-alcohols, or $C_6$ OXO-alcohols, or $C_7$ OXO-alcohols, or $C_8$ OXO-alcohols, including wherein the alkyl residues comprise a mixture of linear and branched alkyl groups.

Advantageously, the alkyl residues have from 0.05 to 0.4 beta branches per residue.

Conveniently, the polymer is selected from the group consisting of vinyl chloride resins, polyesters, polyurethanes, ethylene-vinyl acetate copolymer, rubbers, poly(meth)acrylics and combinations thereof, and is preferably polyvinylchloride.

DETAILED DESCRIPTION

Figure 1:
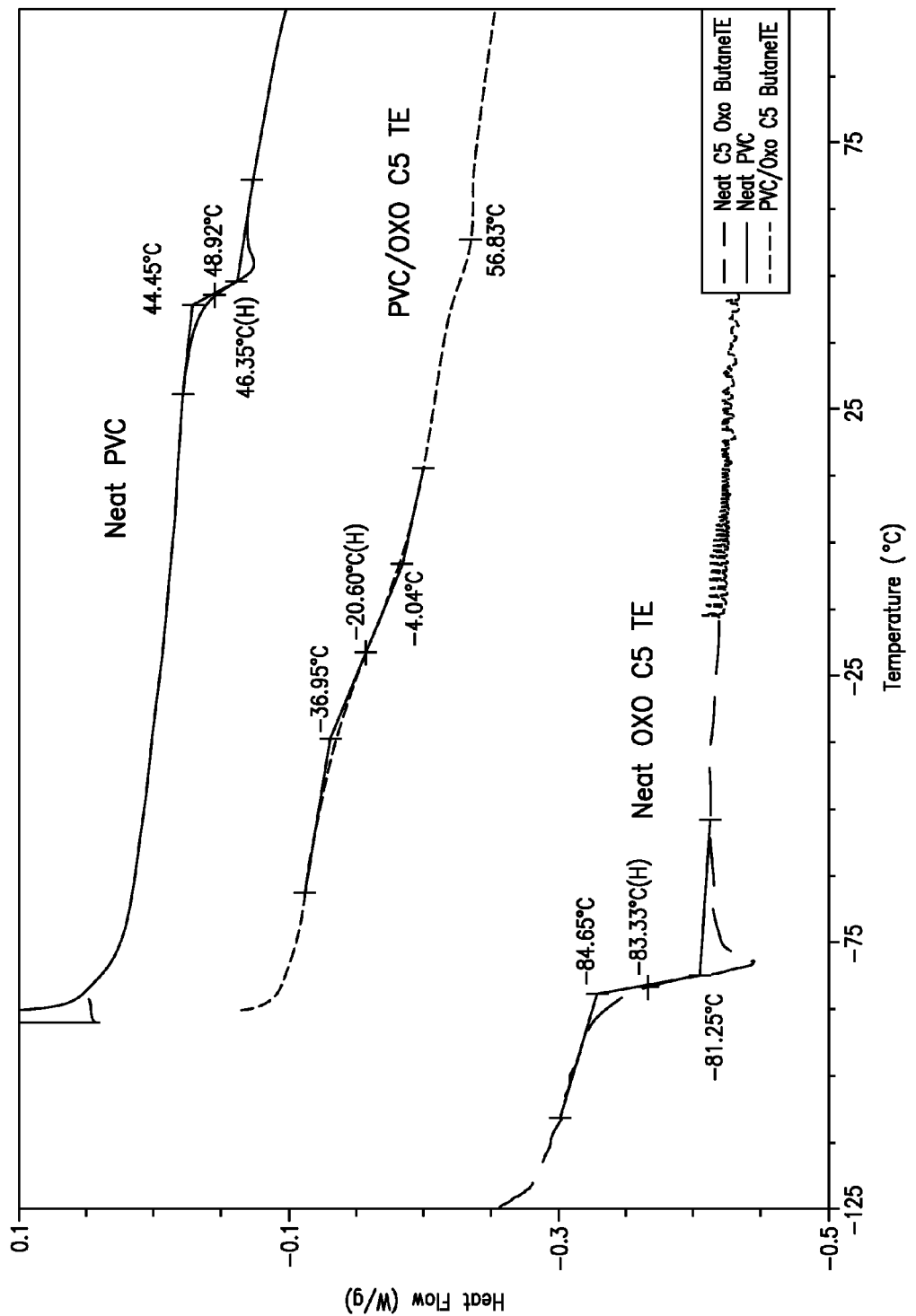
FIG. 1 shows a DSC (differential scanning calorimetry) $T_g$ comparison between neat PVC, the neat OXO $C_5$ butanetetraester plasticizer (Formulation Example 1), and the PVC bar plasticized with the OXO $C_5$ butanetetraester plasticizer.

All numerical values within the detailed description and the claims herein are modified by "about" or "approximately" the indicated value, and take into account experimental error and variations that would be expected by a person having ordinary skill in the art.

There is an increased interest in developing new plasticizers that are non-phthalates and which possess good plasticizer performance characteristics but are still competitive economically. Plasticizer performance is a complex balance of many factors. Optimal performance is achieved not through maximization of one particular property, but by successfully balancing several different properties such as plasticization efficiency, low-temperature properties (glass transition temperature), and permanence (low volatility) to obtain the best overall performance. In many cases, improvement of one property results in a degradation of another property. Thus, successful optimization of performance is often achieved only through complex and unobvious manipulations of plasticizer structures and microstructures. These changes subtly affect the molecular interactions of the plasticizer molecule with the host polymer, through parameters such as free volume, dipole, charge distribution, shape, and the molecular uniformity or non-uniformity of the plasticizer molecules.

Manipulating the uniformity/non-uniformity balance of plasticizers in a formulation is a well-known strategy to optimize plasticization properties, as evidenced by the wide use of commercial plasticizer blends and secondary plasticizers in use today. In such blends, the property balance of the blend may not be a simple additive function of the component plasticizers, but may possess unexpected properties due to synergies between the different components that result in molecular perturbation of the host polymer in a different manner or to a different degree than for single-component plasticizers.

Ester plasticizers are typically prepared using component alcohols or acids of a single chain length, as opposed to mixed chain lengths, due to manufacturing considerations. The alcohol or acid feeds, such as those produced by an olefin carbonylation/oxidation process ("OXO process"), are almost always carried out using olefin feeds of primarily a single carbon number, meaning that other carbon number olefins are present only as very minor components in the feed and do not contribute to its properties with any significance. Although multi-ester plasticizers with mixed carbon number esters are known, their preparation requires additional steps of preparing blended acid or alcohol feeds or using multiple esterification steps. Furthermore, the broad chain length distribution present in multi-ester plasticizers with mixed carbon number sidechains may lead to the presence of some undesirable species in the product mixture, which must be removed by fractional distillation or other additional steps. For example, a triester plasticizer having a mixture of $C_5$ and $C_6$ chains would contain species with three $C_5$ chains, three $C_6$ chains, two $C_5$/one $C_6$ chain, and so forth. The species at the high and low weight ends of the distribution may have less optimal volatility, compatibility, etc. This can only be avoided by adding an additional process step of partially reacting the core precursor with one acid or alcohol to form a partially esterified product, which then must be further esterified with a second acid or alcohol under conditions that do not scramble the sidechain structures, and/or through the use of more complicated or costly protected reagents, such as anhydrides.

Thus, what is needed is a method of producing ester plasticizers with optimized property balances within a more tightly controlled molecular weight window, and from alcohol or ester components having a single carbon number. The authors have unexpectedly found that ester plasticizers featuring branched sidechains composed of mixtures of more than one isomer, even more than two isomers, or even more than three isomers of a single chain length show unexpected performance advantages over similar plasticizers with purely linear, or purely specifically branched, sidechains of analogous carbon number. Larger numbers of isomers are preferable to smaller numbers of isomers, since larger numbers provide a greater continuity between the various structures present and minimize non-synergetic differences or incompatibilities between the structural isomeric extremes present.

The present disclosure is directed towards non-phthalate, tetraester plasticizers, particularly OXO-tetraester plasticizers, that can be made from low cost feeds and employ fewer manufacturing steps in order to meet economic targets. The proposed route to non-phthalate plasticizers of the present disclosure is by esterifying tetracarboxylic acids, such as 1,2,3,4-cyclopentane tetracarboxylic acid or 1,2,3,4-butane-tetracarboxylic acid, with an isomeric mixture of $C_5$, $C_6$, $C_7$, or $C_8$ alcohols.

An "OXO-ester" is a compound having at least one functional ester moiety within its structure derived from esterification of either an acid or alcohol compound with an OXO-alcohol or OXO-acid, respectively.

In one aspect, the present application is directed to a butanetetracarboxylic OXO-ester plasticizer or a cyclopentanetetracarboxylic OXO-ester plasticizer with four saturated sidechains having the same carbon number, in which said sidechains are comprised of at least two or more isomers and preferably three or more isomers. The tetracarboxylic acid is esterified with OXO-alcohols, which are mixed linear and branched alcohol isomers having a single carbon number, the formation of which is described in more detail below.

An "OXO-alcohol" is an organic alcohol, or mixture of isomers of an organic alcohol, which is prepared by hydroformylating an olefin, followed by hydrogenation to form the alcohols. Typically, the olefin is formed by light olefin oligomerization over heterogenous acid catalysts, which olefins are readily available from refinery processing operations. The reaction results in mixtures of longer-chain, branched olefins, which subsequently form longer chain, branched alcohols, as described in U.S. Pat. No. 6,274,756, incorporated herein by reference in its entirety.

An "OXO-acid" is an organic acid, or mixture of organic acids, which is prepared by hydroformylating an olefin, followed by oxidation to form the acids. Typically, the olefin is formed by light olefin oligomerization over heterogenous acid catalysts, which olefins are readily available from refinery processing operations. The reaction results in mixtures of longer-chain, branched olefins, which subsequently form longer-chain, branched acids.

"Hydroformylating" or "hydroformylation" is the process of reacting a compound having at least one carbon-carbon double bond (an olefin) in an atmosphere of carbon monoxide and hydrogen over a cobalt or rhodium catalyst, which results in addition of at least one aldehyde moiety to the underlying compound. U.S. Pat. No. 6,482,972, which is incorporated herein by reference in its entirety, describes the hydroformylation (OXO) process.

Branched aldehydes can be produced by hydroformylation of $C_3$ to $C_{12}$ olefins; in turn, some of these olefins have been produced by propylene and/or butene oligomerization over solid phosphoric acid or zeolite catalysts; for example, $C_9$ olefin isomer mixtures produced by trimerization of propylene. The resulting $C_4$ to $C_{13}$ aldehydes can then be recovered from the crude hydroformylation product stream by fractionation to remove unreacted olefins. These $C_4$ to $C_{13}$ aldehydes are then hydrogenated to alcohols (OXO-alcohols) or oxidized to acids (OXO-acids).

Alternatively, OXO-acids or OXO-alcohols can be prepared by aldol condensation of shorter-chain aldehydes to form longer chain aldehydes, as described in U.S. Pat. No. 6,274,756, followed by oxidation or hydrogenation to form the OXO-acids or OXO-alcohols, respectively. If the shorter-chain aldehydes used comprise multiple isomers, the longer chain aldehydes will similarly comprise multiple isomers of a single carbon number.

As discussed above, the resulting $C_4$ to $C_{13}$ OXO-acids or OXO-alcohols will consist of multiple isomers due to the various isomeric olefins obtained in the oligomerization process, in tandem with the multiple isomeric possibilities of carbon monoxide addition in the hydroformylation step. Such multi-isomeric materials and feeds are typically cheaper than single-isomer feeds and provide a cost advantage for use in further syntheses. The exact isomeric balances may be altered by manipulating the olefins, process parameters, and catalysts used in these steps. For example, a $C_4$ OXO-aldehyde derived from the hydroformylation of propylene may consist of an approximately 65:35 molar mixture of n-butanal and isobutanal. A $C_5$ OXO-aldehyde derived from the hydroformylation of 1-butene may consist of an approximately 65:30:5 ratio of n-valeraldehyde (n-pentanal), 2-methylbutanal, and 3-methylbutanal. A $C_5$ OXO-aldehyde derived from the hydroformylation of 2-butene, or a mixture of 1- and 2-butene, will produce isomeric mixtures with greater percentages of branched isomers. $C_6$, $C_7$, and $C_8$ aldehydes will comprise more complex isomeric distributions. For example, the isomers present in a $C_7$ aldehyde derived from a $C_6$ olefin feed from propylene dimerization may include n-heptanal, 2-methylhexanal, 3-methylhexanal, 4-methylhexanal, 5-methylhexanal, 2-ethylpentanal, 3-ethylpentanal, 2,3-dimethylpentanal, 2,4-dimethylpentanal, 3,3-dimethylpentanal, 3,4-dimethylpentanal, 2,2-dimethylpentanal, and 2,3,3-trimethylbutanal. These isomeric distributions are preserved upon oxidation or reduction to the OXO-acids or OXO-alcohols. All of the isomers present are saturated, i.e., possess no olefinic groups that would lead to undesirable thermal, chemical, or light-promoted crosslinking, oxidation, or other degradative chemical reaction, possess no branching at the carbon bearing the alcohol functionality (i.e., are terminal alcohols (1-ols) rather than internal alcohols (2-ols, 3-ols, etc.), and are acyclic. Cyclic and internal alcohols are not preferred because the presence of branching at such a close position to the ester linkage will reduce the molecular flexibility of the ester linkage, leading to undesirably high viscosities and other features detrimental to plasticizer performance.

The overall isomeric distribution of the OXO-acids or OXO-alcohols may be described quantitatively by parameters such as average branch content per molecule or per chain position. Branching may be determined by Nuclear Magnetic Resonance (NMR) spectroscopy. The OXO-acids or OXO-alcohols used in the present disclosure typically have, on average, between 0.2 and 3.0 total branches per molecule. In some cases, the average branching may range from 0.3 to 1.8 total branches per molecule. In yet other cases, the average branching ranges from 0.2 to 3.0, or from 0.25 to 1.6, or from 0.3 to 1.4 total branches per molecule. According to the present disclosure, OXO-alcohols having from 0.05 to 0.4 branches per molecule at the alcoholic beta carbon (beta branches) are preferred. Tables 1 and 2 present typical branching data for OXO-acids or OXO-alcohols derived from the processes described above.

TABLE 1

¹³C NMR Branching Characteristics of Typical OXO-Alcohols.

| OXO-Alcohol | Avg. Carbon No. | % of α-Carbons w/ Branches[a] | β-Branches per Molecule[b] | Total Methyls per Molecule[c] | Pendant Methyls per Molecule[d] | Pendant Ethyls per Molecule |
|---|---|---|---|---|---|---|
| $C_4$[e] | 4.0 | 0 | 0.35 | 1.35 | 0.35 | 0 |
| $C_5$[f] | 5.0 | 0 | 0.30 | 1.35 | 0.35 | 0 |
| $C_6$ | — | — | — | — | — | — |
| $C_7$ | 7.3 | 0 | 0.15 | 1.96 | 0.99 | 0.04 |
| $C_8$ | 8.6 | 0 | 0.09 | 3.0 | 1.5 | — |
| $C_9$ | 9.66 | 0 | 0.09 | 3.4 | — | — |

— Data not available.
[a] —$\underline{C}$OH carbon.
[b] Branches at the —$\underline{C}$CH$_2$OH carbon.
[c] This value counts all methyl groups, including $C_1$ branches, chain end methyls, and methyl endgroups on $C_{2+}$ branches.
[d] $C_1$ branches only.
[e] Calculated values based on a molar isomeric distribution of 65% n-butanol and 35% isobutanol (2-methylpentanol).
[f] Calculated values based on a molar isomeric distribution of 65% n-pentanol, 30% 2-methylbutanol, and 5% 3-methylbutanol.

TABLE 2

¹³C NMR Branching Characteristics of Typical OXO-Acids.

| OXO-Acid | Average Carbon No. | Pendant Methyls[a] | Total Methyls[b] | Pendant Ethyls | % Carbonyls α to Branch[c] |
|---|---|---|---|---|---|
| $C_4$[d] | 4.0 | 0.35 | 1.35 | 0 | 0.35 |
| $C_5$[e] | 5.0 | 0.35 | 1.35 | 0 | 0.30 |
| $C_6$ | — | — | — | — | — |
| $C_7$ | 6.88-7.92 | 0.98-1.27 | 1.94-2.48 | 0.16-0.26 | 11.3-16.4 |
| $C_8$ | 8.1-8.3 | n/a | 2.7 | n/a | 12-15 |
| $C_9$ | 9.4 | n/a | n/a | n/a | 12 |

[a] $C_1$ Branches only.
[b] Includes methyls on all branch lengths and chain end methyls.
[c] The "alpha" position in the acid nomenclature used here is equivalent to the alcohol "beta" carbon in Table 1.
[d] Calculated values based on a molar isomeric distribution of 65% n-butanoic acid and 35% isobutanoic acid (2-methylpentanoic acid).
[e] Calculated values based on a molar isomeric distribution of 65% n-pentanoic acid, 30% 2-methylbutanoic acid, and 5% 3-methylbutanoic acid.

"Esterifying" or "esterification" is reaction of a carboxylic acid moiety with an organic alcohol moiety to form an ester linkage. Esterification conditions are well known in the art and include, but are not limited to, temperatures of 0-300° C., and the presence or absence of homogeneous or heterogeneous esterification catalysts such as Lewis or Brønsted acid catalysts.

One potential route to non-phthalate plasticizers is by forming 1,2,3,4-cyclopentane tetracarboxylic acid via the well known Diels-Alder reaction of cyclopentadiene with maleic anhydride. The product, bicyclo[2.2.1]hept-5-ene-2,3-dicarboxylic anhydride, may be oxidized with such as nitric acid, ozone, ruthenium tetraoxide or other oxidation catalysts to yield the tetracarboxylic acid of cyclopentane. For example:

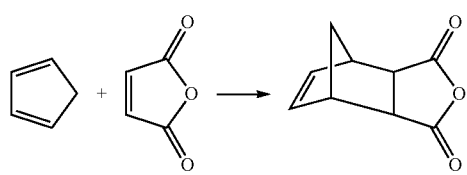

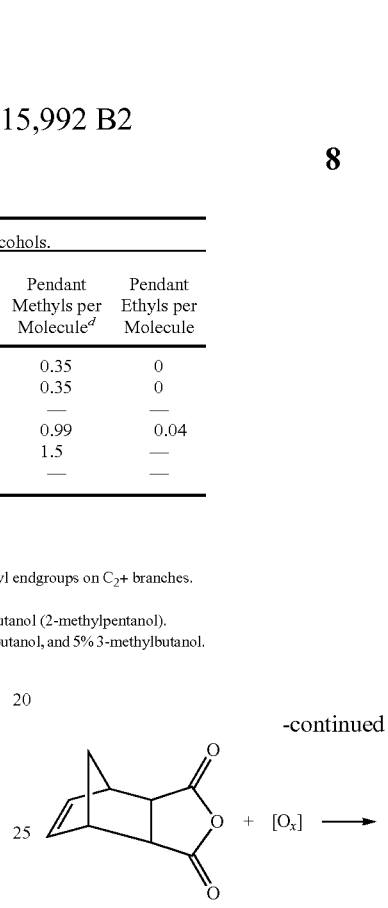

Then the cyclopentane tetracarboxylic acid can be esterified in the normal manner using plasticizer-range OXO-alcohols (ROH):

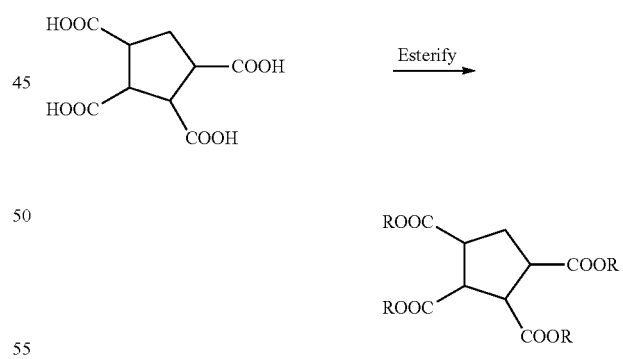

wherein each R is the alkyl residue of a $C_5$ to $C_8$ OXO-alcohol isomeric mixture. Cis,cis,cis,cis-1,2,3,4-cyclopentanedicarboxylic acid may be used, or other isomer or isomeric mixture containing cis/trans or trans positionings of the acid groups.

In another embodiment, 1,2,3,4-butanetetracarboxylic acid is produced via Diels-Alder reaction of butadiene with maleic anhydride to form 4,5-cyclohexene dicarboxylic acid anhydride, which is then oxidized with such as nitric acid, ozone or oxidative cleavage with hydrogen peroxide in the presence of heteropolyacids or other oxidation catalysts.

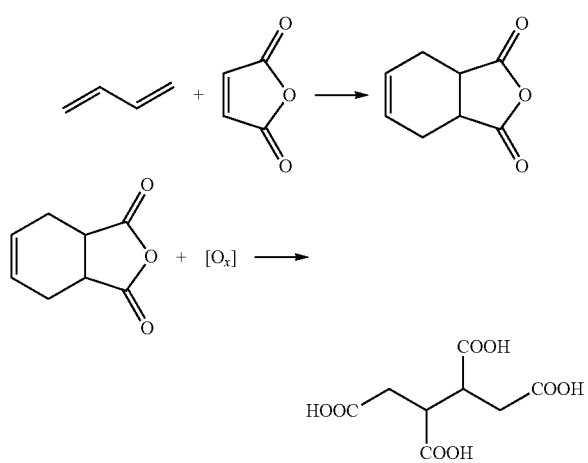

Subsequently, the tetracarboxylic acid is esterified in the normal manner using plasticizer-range OXO-alcohols (ROH).

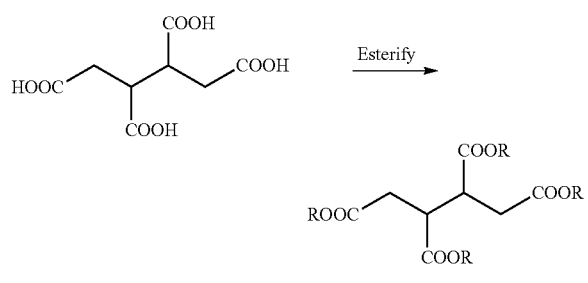

wherein each R is the alkyl residue of a $C_5$ to $C_8$ OXO-alcohol isomeric mixture. Any of the enantiomers or diastereomers, including mixtures, of 1,2,3,4-butanetetracarboxylic acid may be used.

We have found that when $C_5$ to $C_8$ OXO-alcohols are used as reactants for the esterification reactions described above, the resulting OXO-esters, having isomeric sidechain distributions of a single carbon number alcohol residue, are in the form of relatively high-boiling liquids (having low volatility), which are readily incorporated into polymer formulations as plasticizers, and possess the unexpected performance advantages described previously. The overall isomeric distribution of the tetraester plasticizers is a function of the OXO-alcohols used in their preparation. The plasticizers have, on average, between 0.2 and 3.0 total branches per each $C_5$-$C_8$ sidechain group (alkyl residue). In some cases, the average branching may range from 0.3 to 1.8 total branches per group. In yet other cases, the average branching ranges from 0.2 to 3.0, or from 0.25 to 1.6, or from 0.3 to 1.4 total branches per group. The average branching per tetraester will equal four times the average branching per group, since each tetraester bears four sidechain groups. The sidechain groups have, on average, from 0.05 to 0.4 beta branches per group (alkyl residue).

In a first embodiment, the present disclosure is directed to tetraesters of a $C_4$-$C_5$ aliphatic tetracarboxylic acid, such as 1,2,3,4-butanetetracarboxylic acid or 1,2,3,4-cyclopentanetetracarboxylic acid, and OXO-alcohols.

In a preferred embodiment, the ester moieties are mixed-isomer alkyl residues of $C_5$ to $C_8$ OXO-alcohols, advantageously mixed-isomer alkyl residues of $C_5$ OXO-alcohols, or $C_6$ OXO-alcohols, or $C_7$ OXO-alcohols, or $C_8$ OXO-alcohols, including wherein the alkyl residues comprise a mixture of linear and branched alkyl groups.

Advantageously, the alkyl residues have from 0.05 to 0.4 beta branches per residue.

In another embodiment, the present disclosure is directed to a plasticizer compound of the formula:

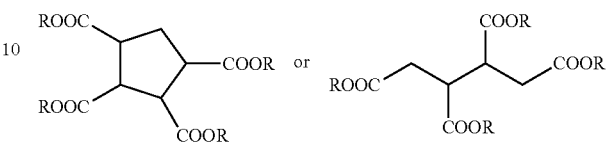

wherein each R is the alkyl residue of $C_5$ to $C_8$ OXO-alcohols, such as wherein collectively R represents mixed-isomer alkyl residues of $C_5$ to $C_8$ OXO-alcohols, preferably wherein each R is the alkyl residue of $C_5$ to $C_7$ OXO-alcohols, and more preferably wherein collectively R represents mixed-isomer alkyl residues of $C_5$ OXO-alcohols, or $C_6$ OXO-alcohols, or $C_7$ OXO-alcohols, or $C_8$ OXO-alcohols, including wherein the alkyl residues comprise a mixture of linear and branched alkyl groups.

Advantageously, the alkyl residues have from 0.05 to 0.4 beta branches per residue.

In a further embodiment, the disclosure is directed to a composition comprising a polymer and a plasticizer of the formula:

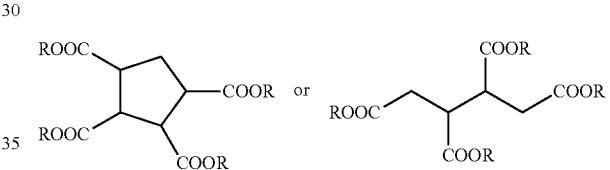

wherein each R is the alkyl residue of $C_5$ to $C_8$ OXO-alcohols, such as wherein collectively R represents mixed-isomer alkyl residues of $C_5$ to $C_8$ OXO-alcohols, preferably wherein each R is the alkyl residue of $C_5$ to $C_7$ OXO-alcohols, and more preferably wherein collectively R represents mixed-isomer alkyl residues of $C_5$ OXO-alcohols, or $C_6$ OXO-alcohols, or $C_7$ OXO-alcohols, or $C_8$ OXO-alcohols, including wherein the alkyl residues comprise a mixture of linear and branched alkyl groups.

Advantageously, the alkyl residues have from 0.05 to 0.4 beta branches per residue.

Conveniently, the polymer is selected from the group consisting of vinyl chloride resins, polyesters, polyurethanes, ethylene-vinyl acetate copolymer, rubbers, poly(meth)acrylics and combinations thereof, and is preferably polyvinylchloride.

EXAMPLES

The following examples are meant to illustrate the present disclosure and inventive processes, and provide where appropriate, a comparison with other methods, including the products produced thereby. Numerous modifications and variations are possible and it is to be understood that within the scope of the appended claims, the disclosure may be practiced otherwise than as specifically described herein.

Comparative Examples 1-2 and Formulation Example 1 provide a behavioral comparison between the multi-isomer OXO-tetraester plasticizers of the current disclosure and similar chain length species comprising only one branched or linear isomer. This comparison illustrates the improved property balance seen with multi-isomer OXO-derived tetraesters. Specific comments are given after the individual examples. Formulation Examples 2-3 and Comparative Examples 3-4 provide additional examples of other OXO and non-OXO tetraester plasticizers.

Gas chromatography (GC) analysis on the products was conducted using a Hewlett-Packard 5890 GC equipped with a HP6890 autosampler, a HP flame-ionization detector, and a J&W Scientific DB-1 30 meter column (0.32 micrometer inner diameter, 1 micron film thickness, 100% dimethylpolysiloxane coating). The initial oven temperature was 60° C.; injector temperature 290° C.; detector temperature 300° C.; the temperature ramp rate from 60 to 300° C. was 10° C./minute with a hold at 300° C. for 14 minutes. The calculated %'s reported for products were obtained from peak area, with an FID detector uncorrected for response factors. GC/FIMS (gas chromatography/time-of-flight field ionization mass spectrometry) was conducted using an Agilent 6890 GC equipped with a 30 meter J&W Scientific DB-1 column (0.25 micron dimethylsiloxane film thickness, 0.25 mm inner diameter) and a MicroMass GCT mass spectrometer. $CS_2$ or $CH_2Cl_2$ was used as the injection solvent. GC oven temperature was ramped from 35 to 350° C. (temperature of GC-MS interface) at 10° C./minute. Viscosity was measured in centiPoise (cP) using a cone-and-plate Anton Paar (25 mm) viscometer (sample size ~0.1 mL).

Comparative Example 1

Synthesis of 1,2,3,4-butanetetracarboxylic acid tetraester of 2-methylbutanol(tetrakis(2-methylbutyl)butane)-1,2,3,4-tetracarboxylate)

A 500 mL 4-necked round-bottom flask was fitted with a stirbar, mechanical stirring shaft with semicircular glass blade, thermometer adapter, and a 25 mL Dean-Stark trap topped with a water-cooled condenser. 1,2,3,4-Butanetetracarboxylic acid (60 g, 256 mmol uncorrected for purity; Aldrich Chemical Co., 99%), 2-methyl-1-butanol (99.29 g, 1.126 mol, 4.4 eq.; Aldrich Chemical Co.), 50 mL xylenes, and 50 mL distilled $H_2O$ were added. [The tetraacid was soluble in water but not in xylenes or 2-methyl-1-butanol; water was added to prevent an initially heterogeneous reaction.] The two-phase solution was heated and stirred at reflux under $N_2$ (88-115° C.) until 40 mL $H_2O$ was collected in the Dean-Stark trap. The solution was cooled to room temperature overnight and then re-heated to reflux the next morning until an additional 10 mL of $H_2O$ (50 mL total) was collected. Immediately, a solution of titanium(IV) isopropoxide (478 mg, 1.68 mmol; 0.3 wt % of combined reagents) in 5 mL xylenes was added. After an additional 16 h at reflux, an additional 18 g of $H_2O$ was collected in the Dean-Stark trap (theoretical amount=18.45 g). The resultant one-phase solution was cooled and depleted of volatiles using a rotary evaporator and high vacuum (~1×10$^{-3}$ mm Hg) to give 126 g (95.6%) of a clear golden yellow liquid (yellow color ascribed to Ti residues). Attempted distillation of a 36 g portion under dynamic high vacuum resulted in discoloration with no resultant distillate even at 220° C. A 5 mL aliquot of the crude material was more rigorously dried under high vacuum at 70° C. overnight for NMR, IR, GC, GC/FIMS, and thermal characterization. A 15.9 g portion of the remaining crude was passed through a large silica column using $CH_2Cl_2$ as eluent. Several cuts were collected which showed no major spectral differences from each other or from vacuum-dried material. The combined cuts (8.2 g of a pale yellow liquid, 97.2-97.5% purity by GC) were used for plasticizer testing as described in Evaluation Example 1 and following. $^1$H NMR (400 MHz, CDCl$_3$: δ 3.91 and 3.82 (complex m, each 4H, OCH$_2$), 3.30 (complex d, app J=11.2 Hz, 2H, CHC(=O)—), 2.76 (br d of d, J=16.8 and 9.2 Hz) and 2.37 (br d of d, J=16.8 and 3.6 Hz) (each 2H, CH$_2$C(=O)—), 1.64 (app. sextet, J=6.2 Hz), 1.36 (br m), and 1.12 (app. septet, J=7.2 Hz) (each 4H, CHMe and CH$_2$Me), 0.86 (superimposed tr, appx. J=3.4 Hz) and 0.83 (superimposed d, appx. J=8.0 Hz) (24H, CHMe and CH$_2$Me). Minor peaks possibly representing the diester impurity were seen at 2.82, 2.42, and 1.26. $^{13}$C NMR (125 MHz, CDCl$_3$, confirmed by DEPT-135): δ 171.30 (CHC(=O)—), 171.20 (CH$_2$C(=O)—) (minor peaks at 172.14, 171.34, and 171.29 may correspond to diester/isomers), 69.85 and 69.43 (OCH$_2$, minor peak at 69.37), 42.27 (CHC(=O)—, minor peak at 42.20), 33.94 and 33.89 (CHMe), 33.24 (CH$_2$C(=O)—, minor peak at 33.13), 25.85 (CH$_2$Me, secondary peak at 25.82), 16.23 (CHMe, minor peak at 16.20), 11.04 (CH$_2$Me, secondary peaks at 11.08 and 11.01). The exact nature of the secondary peaks in the spectrum (whether due to the presence of diastereomers or a diacid impurity) was not determined. IR (thin film on NaCl): 2959 (s), 2932 (sh), 2875 (m), 1736 (vs, $v_{C=O}$), 1463 (m), 1410 (sh), 1392 (w), 1378 (w), 1337 (w), 1259 (m), 1165 (s, $v_{C-O}$), 1108 (w), 1041 (w), 997 (w), 772 (w) cm$^{-1}$. GC/FIMS: m/z 514 (M$^+$, 100; calcd. 514.35), 374 (diester, 8; calcd. 374.19). Purity by GC analysis (uncorrected for response factor): 92% (main peak attributed to product; an unidentified near-overlapping peak was observed at slightly longer retention time that may represent an isomeric species giving rise to NMR spectrum complexities; 2.8%).

Formulation Example 1

Synthesis of 1,2,3,4-butanetetracarboxylic acid tetraester of n-pentanol/2-methylbutanol/3-methybutanol mixture Using a procedure similar to that described in Comparative Example 1, 1,2,3,4-butanetetracarboxylic acid (60 g, 256 mmol) was reacted with a mixture of 65 g (681 mmol) 1-pentanol, 30 g (340 mmol) 2-methylbutanol, and 5 g (57 mmol) 3-methylbutanol (typical of the isomeric distribution of a C$_5$-OXO-alcohol). The solution was cooled to 70° C. rather than to room temperature overnight prior to the additional 16 hours of reflux. A 128 g (97%) portion of a cloudy dark orange liquid was collected after devolatilization at 70° C. under high vacuum overnight. This material was observed to precipitate small amounts of a white wax/haze at its surface over time. A 25 g portion was decolorized by stirring over 1 g of carbon black at 120° C. for 2 hours followed by filtration. The resultant clear, light yellow material (which did not precipitate any white solids) was devolatilized under high vacuum at 100° C. overnight. $^1$H NMR for crude product (CDCl$_3$, 400 MHz): δ 4.13-4.02 (m, major portion is q at 4.62, J=6.0; pentyl OCH$_2$ overlaid with 3-methylbutyl OCH$_2$), 3.96 and 3.86 (each m, 2-methylbutyl OCH$_2$), 3.30 (br tr, butyl backbone CH), 2.79 (br app d of d) and 2.39 (br d of d, J=16.8 and 3.6 Hz) (butyl backbone CH$_2$), 1.67 (br tr, 2-methylbutyl CH or one H of CH$_2$), 1.60 (br tr, J=5.8 Hz, one pentyl CH$_2$ group) (3-methylbutyl CH hidden underneath peaks at 1.67-1.60), 1.49 (q, J=6.9, 3-methylbutyl CH$_2$), 1.40 (m, 2-methylbutyl CH or one H of CH$_2$), 1.31 (two pentyl CH$_2$ groups), 1.16 (theo. septet, J=7.3 Hz, 2-methylbutyl CH or one H of CH$_2$), 0.89 (br tr, J=6.6, pentyl Me) (2-methylbutyl CHMe, CH$_2$Me, and 3-methylbutyl CHMe$_2$, hidden under peak at 0.89). $^{13}$C NMR for crude product (CDCl$_3$, 125 MHz, assigned by DEPT-135): δ 172.21 (minor), 172.09 (splits upon further drying), 171.44 (minor), 171.39 (splits upon further drying) (C=O; not possible to determine if minor peaks are from residual less-substituted esters or minor tetraester isomers); 69.89 and 69.50 (2-methylbutyl OCH$_2$, 27.8% of total), 65.35 and 65.01 (pentyl OCH$_2$, 68.3% of total), 63.85 and 63.52 (3-methylbutyl OCH$_2$, 3.9% of total), 42.32 (butane backbone CH), 37.15 and 37.07 (3-methylbutyl CH$_2$), 33.99 and 33.94 (2-methylbutyl CH), 33.37 (minor) and 33.29 (butane backbone CH$_2$), 28.16 and 28.09 (pentyl CH$_2$), 27.93 and 27.91 (pentyl CH$_2$), 25.91 and 25.87 (minor) (2-methylbutyl CH$_2$), 24.94 and 24.89 (3-methylbutyl CH), 22.37 and 22.34 (3-methylbutyl CH$_3$), 22.23 and 22.22 (pentyl CH$_2$), 16.29 and 16.26 (2-methylbutyl CH$\underline{Me}$), 13.86 (pentyl Me), 11.13, 11.10, and 11.07 (2-methylbutyl CH$_2$$\underline{Me}$). IR (thin film on NaCl): 19.60 (s), 29.34 (s), 2874 (m), 1737 (vs), 1466 (m), 1410 (sh), 1394 (m), 1380 (m), 1338 (m), 1260 (s), 1169 (s), 1073 (w), 1047 (m), 982 (m), 875 (w), 775 (w), 730 (w) cm$^{-1}$. Purity: 99.9% (GC-FID, uncorrected for response factor). GC-TOF-FIMS: m/z 514.3524 (M$^+$; 100%, calc. 514.3506).

Comparative Example 2

Synthesis of 1,2,3,4-butanetetracarboxylic acid tetraester of n-pentanol(tetrapentylbutane-1,2,3,4-tetracarboxylate)

A 250 mL 4-necked round-bottom flask was fitted with a stirbar, mechanical stirring shaft with semicircular glass blade, thermometer adapter, and a 25 mL Dean-Stark trap topped with a water-cooled condenser. 1,2,3,4-Butanetetracarboxylic acid (30 g, 128 mmol, Aldrich Chemical Co., 99%), n-pentanol (50 g, 570 mmol, 4.4 eq.; Aldrich Chemical Co.), 25 mL xylenes, and 25 mL distilled H$_2$O were added. The Dean-Stark trap was filled with an additional 23.8 g of pentanol. The two-phase solution was heated and became homogeneous at 85° C. The solution was stirred at reflux (115° C.) for 4 hour; 23 mL H$_2$O was collected in the Dean-Stark trap. A solution of titanium(IV) isopropoxide (289 mg, 1.02 mmol; 0.3 wt % of combined reagents) in 5 mL xylenes was added and the solution was stirred for 17 hours at 145° C. A second 289 mg aliquot of titanium(IV) isopropoxide was added and the solution was stirred for an additional 16 hours at 150° C. Volatiles were removed from the crude product by distillation in a Kugelrohr apparatus at 100° C./0.7 mm Hg. The residual product (~54 g, 82%) was stirred for 2 hours at room temperature over 2 g Darco G60-100 mesh activated charcoal, then filtered through Celite. $^1$H NMR (CDCl$_3$, 400 MHz): δ 4.05 (q, J=6.2 Hz, 8H, OCH$_2$), 3.28 (complex d, J=6.6 Hz, 2H, CH(C=O)—), 2.78 (d, J=9.4 Hz) and 2.74 (d, J=9.3 Hz) (2H) and 2.40 (d, J=3.8 Hz) and 2.36 (d, J=3.7 Hz) (2H) (CH$_2$(C=O)—), 1.59 (br m, 8H) and 1.30 (br m, 16H) (CH$_2$), 0.88 (tr, J=6.3 Hz, 12H, CH$_3$). $^{13}$C NMR (CDCl$_3$, 125 MHz, assigned by DEPT-135): δ 172.06 and 171.33 (4C, C=O), 65.30 and 64.96 (4C, OCH$_2$), 42.30 (2C, $\underline{C}$H(C=O)—), 33.26 (2C, $\underline{C}$H$_2$(C=O)—), 28.13, 28.07, 27.90, 27.88 (total 8C, CH$_2$), 22.19 (4C, $\underline{C}$H$_2$Me), 13.82 (4C, CH$_3$). Minor C=O resonances, possibly representing incompletely esterified species, were present at 172.17 and 171.40 ppm (<7.1% of C=O integral). IR (thin film on NaCl): 2958 (vs), 2933 (s), 2873 (m), 2862 (m), 1741 (vs), 1738 (vs), 1730 (sh), 1467 (m), 1459 (sh), 1436 (vw), 1412 (w), 1394 (m), 1380 (w), 1338 (m), 1260 (m), 1224 (m), 1169 (vs), 1122 (vw), 1109 (vw), 1074 (w), 1048 (m), 1021 (vw), 980 (m), 875 (w), 830 (w), 776 (w), 730 (w) cm$^{-1}$. Purity: 99.3% (GC-FID, uncorrected for response factor). (Not analyzed by GC-TOF-FIMS).

Comparative Example 3

Synthesis of 1,2,3,4-butanetetracarboxylic acid tetraester of C$_9$ OXO-alcohol isomer mixture Using a procedure similar to that described in Comparative Example 1, 1,2,3,4-butanetetracarboxylic acid (60 g, 256 mmol) was reacted with 162.5 g (1.13 mol) of an isomeric mixture of C$_9$ OXO-alcohols (ExxonMobil Exxal™ 9; containing no branches α to the OH functionality). After collection of the initial 50 mL added H$_2$O at 85-120° C. and addition of the Ti catalyst, ~19 mL of H$_2$O was collected over a 4 h period. The pot temperature at the end of the reaction reached 170° C. A 193.5 g portion (~100%; theo. yield 189.2 g) of a cloudy dark orange liquid was collected after devolatilization at 70° C. under high vacuum overnight. This material was observed to precipitate small amounts of a white wax/haze at its surface over time. A 25 g portion was decolorized by stirring over 1 g of carbon black at 120° C. for 2 hours followed by filtration. The resultant clear, light yellow material (which did not precipitate any white solids) was devolatilized under high vacuum at 100° C. overnight. GC analysis of the product was unsuccessful to gauge purity due to its high molecular weight. However, analysis of the decolorized material suggested the presence of residual alcohol or other lower molecular weight species. High vacuum devolatilization was performed at 100° C. overnight on the decolorized material to remove any residual volatiles. $^1$H NMR (CDCl$_3$, 400 MHz): δ 11-4.03 (m, 8H, ester chain OCH$_2$), 3.85-3.78 (m, minor, may represent OCH$_2$ near branches or residual di- or triester OCH$_2$), 3.29 (br, 2H, butane backbone CH), 2.84 (minor sh to 2.77 cluster), 2.77 (br q, 2H, butane backbone CH$_2$), 2.44 (minor sh to 2.38 d), 2.38 (br d, J=16.4 Hz, 2H, butane backbone CH$_2$), 1.73-0.94 (br m with major resonances at 1.60, 1.27, 1.11, ester chain CH and CH$_2$), 0.93-0.71 (br m, major resonance at 0.84, ester chain CH$_3$) (combined 68H). $^{13}$C NMR (CDCl$_3$, 125 MHz, assigned by DEPT-135): δ 172.18 (minor), 172.06, 171.41 (minor), 171.33 (C=O; not possible to determine if minor peaks are from residual less-substituted esters or minor tetraester isomers), 65.66, 65.31, 64.99, 64.30 (minor), 63.82, 63.78, 63.43, 63.38 (ester chain OCH$_2$), 46.64-8.29 (ester chain and butane backbone CH, CH$_2$, CH$_3$; major butane backbone carbon resonances appear at 42.29 (CH) and 33.26 (CH$_2$). IR (thin film on NaCl): 2958 (s), 2929 (s), 2872 (m), 1739 (vs), 1465 (m), 1411 (w), 1380 (m), 1366 (m), 1337 (m), 1256 (sh), 1217 (sh), 1168 (s), 1042 (w), 990 (w) cm$^{-1}$. GC-TOF-FIMS: 739.2549 (M$^+$; calc. 739.12, 100%). ESI-MS: m/z 739 (M+H$^+$; calc. 739.12, 82%), 756.1 (M+18$^+$, 100%), other peaks associated with longer ester chains (770, 784). GC analysis on the product was unsuccessful; the product appeared as a large smear eluting over several minutes (residual lights were observed but may appear more prevalent than actually present, and could not be quantified).

Comparative Example 4

Synthesis of cis,cis,cis,cis-1,2,3,4-cyclopentanetetracarboxylic acid tetraester of 2-methylbutanol(tetrakis (2-methylbutyl)cyclopentene-1,2,3,4-tetracarboxylate)

Cis,cis,cis,cis-1,2,3,4-cyclopentanetetracarboxylic acid (30 g, 122 mmol) and 2-methyl-1-butanol (47.24 g, 540 mmol) were mixed in 10 mL xylenes in a 250 mL 4-necked round-bottomed flask. The mixture was still inhomogeneous after stirring for 30 minutes at room temperature. It was subsequently heated to reflux (~140° C.) and a solution of titanium tetraisopropoxide (232 mg, 0.82 mmol, 0.3 wt % of reactants) in 5 mL xylenes was added. After a total of 16 hours at reflux, 8 g of $H_2O$ was collected in the Dean-Stark trap (theo. 8.79 g=8.79 mL). NMR analysis of an aliquot of reaction product showed unreacted acid groups. A second 116 mg (0.41 mmol) aliquot of Ti catalyst in 2.5 mL xylenes was added and the pot temperature was increased to 155° C. for 5 hours. No additional water was collected. After removal of xylenes, the residue (40 g, 62%) was devolatilized under high vacuum at 100° C. for 5 hours. A Kugelrohr distillation of a ~12 g portion of this material was carried out at 121° C./4.4× $10^{-4}$ torr, discarding ~2 g of initial distillate; however, product of greater purity was not obtained. A second ~15 g portion of the residue was eluted through a silica column using $CH_2Cl_2$ as the eluent ($R_f$~0.55); fractions were monitored by gas chromatography. Combined middle fractions gave 7 g of high purity product used for plasticization tests. A repeat synthesis was performed in the absence of solvent: cis,cis,cis, cis-1,2,3,4-cyclopentanetetracarboxylic acid (10 g, 41 mmol) and 2-methyl-1-butanol (21.5 g, 24.4 mmol) were mixed in a 50 mL 2-necked round-bottom flask with a magnetic stirbar, Dean-Stark trap, and thermometer. An additional 4.95 g of 2-methyl-1-butanol was loaded into the Dean-Stark trap (below the level of return to flask) to prevent its depletion in the reaction flask. The contents of the flask were heated at reflux (127-140° C.) for 16 hours and water was collected. The resultant crude material (not weighed) was distilled under vacuum using a Kugelrohr apparatus in two portions (5 g portion yielding 2.3 g and remainder yielding 9.49 g). GC and GCMS analysis of these distillates indicated some residual diester species. The materials were not further purified via column chromatography. $^1H$ NMR, small Kugelrohr distillate from $2^{nd}$ solvent-free preparation ($CDCl_3$, 400 MHz): δ 4.04-3.76 (m, 8H, $OCH_2$), 3.68 (tr, 1H, J=8.4 Hz) and 3.41 (tr, 1H, J=8.2 Hz) (ring CHC(C=O)— away from ring $CH_2$), 3.21 (q, 1H, J=7.8 Hz) and 3.10 (q, 1H, J=8.7 Hz) (ring C HC(C=O)— next to ring $CH_2$), 2.42-2.35 (m, 2H, ring $CH_2$), 1.75-1.60 (m, 4H), 1.46-1.33 (m, 4H), and 1.16 (app sextet, J=7.2 Hz, 4H) (sidechain CHMe and $CH_2$Me, 0.92-0.85 (m, 24H, sidechain CHMe and $CH_2$Me). Minor resonances at 3.64-3.45, 2.8-2.6, 2.3, and 2.05 ppm may represent minor isomers. $^{13}C$ NMR, small Kugelrohr distillate from $2^{nd}$ solvent-free preparation ($CDCl_3$, 125 MHz, assigned by DEPT-135): δ 173.41, 173.03, 172.65, 172.48 (C=O), 69.85, 69.73, 69.68, 69.62 ($OCH_2$), 49.73, 48.99, 46.77, 45.90 (ring CHC(C=O)—), 34.03, 33.92 (CHMe), 32.22 (ring $CH_2$), 25.90, 25.87, 25.85 ($CH_2$Me), 16.26, 16.23 (CHMe), 11.10 ($CH_2$Me). IR of product from column chromatography (thin film on NaCl): 2963 (vs), 2927 (sh), 2878 (m), 1736 (vs), 1464 (m), 1398 (sh), 1380 (m), 1261 (s), 1189 (vs), 1040 (sh), 1002 (m), 951 (w), 772 (w) $cm^{-1}$. Purity after column chromatography: 99.8% with four major isomer peaks (GC-FID, uncorrected for response factor). GC-TOF-FIMS, small Kugelrohr distillate from $2^{nd}$ solvent-free preparation (prior to final purification): m/z 526.7 ($M^+$; 100%, calc. 526.35); 368.4 (diester with remaining two acid groups converted into anhydride, 30%, calc. 368.18).

Formulation Example 2

Synthesis of 1,2,3,4-butanetetracarboxylic acid tetraester of $C_7$ OXO-alcohol isomer mixture A 250 mL 4-necked round-bottom flask was fitted with a stir bar, mechanical stirring shaft with semicircular glass blade, thermometer adapter, and a 25 mL Dean-Stark trap topped with a water-cooled condenser. 1,2,3,4-Butanetetracarboxylic acid (30 g, 128 mmol, Aldrich Chemical Co., 99%), Exxal 7 alcohols (isomeric mixture, 66 g, 567 mmol, 4.4 eq.; ExxonMobil Chemical Co.), 25 mL xylenes, and 25 mL distilled $H_2O$ were added. The Dean-Stark trap was filled with an additional 31.4 g of Exxal 7. The two-phase solution was heated and became homogeneous at 85° C. The solution was stirred at reflux (105° C.) for 4 hours; 25 mL $H_2O$ was collected in the Dean-Stark trap. A solution of titanium(IV) isopropoxide (289 mg, 1.02 mmol; 0.3 wt % of combined reagents) in 5 mL xylenes was added and the solution was stirred for 3 hours at 145° C., resulting in the retrieval of 7.5 mL (81% of theo.) of water. Volatiles were removed from the crude product by distillation using a short path distillation apparatus at 80° C./0.1 mm Hg. Residual volatiles were removed under vacuum at 100° C./0.1 mm Hg for several hours. The residual product (~75 g, 94%) was stirred for 2 hours at 100° C. over 3 g of activated carbon, then filtered through a packed bed of Celite to yield 56 g (69%) of clear, colorless liquid. $^1H$ NMR ($CDCl_3$, 400 MHz): δ 4.02-3.95 (m, 8H, ester chain $OCH_2$), 3.91-3.87 and 3.79-3.70 (m, minor, may represent $OCH_2$ near beta-branches or residual di- or triester $OCH_2$), 3.21 (br m, 2H, butane backbone CH), 2.68 (br q, 2H, butane backbone $CH_2$), 2.33 and 2.29 (d, J=15.2 Hz, 2H, butane backbone $CH_2$), 1.60-1.06 (br m with major resonances at 1.52, 1.22, 1.11, ester chain CH and $CH_2$), 0.71 (apparent tr, J=16.4 Hz, ester chain $CH_3$). $^{13}C$ NMR ($CDCl_3$, 125 MHz, assigned by DEPT-135): δ 171.90 (minor, overlapped with next peak), 171.79, 171.10 (minor, overlapped with next peak), 171.04 (C=O; not possible to determine if minor peaks are from residual, less-substituted esters or minor tetraester isomers; minor peaks represent 10.9% of total C=O integral), 70.14, 69.89, 69.78, and 69.50 (cluster of 4 minor peaks), 67.15 and 66.87 (cluster of 2 minor peaks), 65.37 (minor), 65.03 and 64.68 (major), 63.83 (minor), 63.47 and 63.11 (major) (ester chain $OCH_2$; minor peaks may represent residual, less-substituted esters or minor tetraester isomers), 46.29-10.37 (ester chain and butane backbone CH, $CH_2$, $CH_3$; butane backbone CH carbon identified at 42.09). IR (thin film on NaCl): 3449 (w, may be residual $CO_2H$ O—H stretch), 2957 (s), 2930 (s), 2871 (m), 1738 (vs, $v_{C=O}$), 1463 (m), 1366 (m), 1331 (m), 1256 (w), 1168 (s), 1006 (vw) $cm^{-1}$. GC/FIMS: m/z 626 ($M^+$, 100; calcd. 626.51). Purity by GC analysis (uncorrected for response factor): 98.8%.

Formulation Example 3

Synthesis of 1,2,3,4-butanetetracarboxylic acid tetraester of $C_8$ OXO-alcohol isomer mixture A 250 mL 4-necked round-bottom flask was fitted with a stir bar, mechanical stirring shaft with semicircular glass blade, thermometer adapter, and a 25 mL Dean-Stark trap topped with a water-cooled condenser. 1,2,3,4-Butanetetracarboxylic acid (30 g, 128 mmol, Aldrich Chemical Co., 99%) Exxal 8 alcohols (isomeric mixture, 67 g, 514 mmol, 4.0 eq.; ExxonMobil Chemical Co.), 25 mL xylenes, and 25 mL distilled $H_2O$ were added. The Dean-Stark trap was filled with an additional 20 mL of Exxal 8. The two-phase solution was heated and became homogeneous at 85° C. The solution was stirred at reflux (105° C.) for 4 hours; 25 mL $H_2O$ was collected in the Dean-Stark trap. A solution of titanium(IV) isopropoxide (289 mg, 1.02 mmol; 0.3 wt % of combined reagents) in 5 mL xylenes was added and the solution was stirred for 4 hours at 145° C. A second charge of titanium(IV) isopropoxide (289 mg, 1.02 mmol; 0.3 wt % of combined reagents) in 5 mL xylenes was added, along with 20 mL of additional Exxal 8. The solution was stirred for 4 hours at 145° C., resulting in the retrieval of 8.5 mL (92% of theo.) of water. Volatiles were removed from the crude product by distillation using a short path distillation apparatus at 80° C./0.1 mm Hg. Residual volatiles were removed under vacuum at 100° C./0.1 mm Hg for several hours. The residual product (~83 g, 95%) was stirred for 2 hours at 100° C. over 4 g of activated carbon, then filtered through a packed bed of Celite, resulting in ~53 g (60%) of clear, light amber colored liquid. $^1$H NMR (CDCl$_3$, 400 MHz): δ 4.00-3.96 (m, 8H, ester chain OCH$_2$), 3.89 and 3.76-3.69 (m, minor, may represent OCH near branches or residual di- or triester OCH$_2$), 3.19 (br, 2H, butane backbone CH), 2.70-2.66 (br. q, 2H, butane backbone CH$_2$), 2.31 and 2.27 (d, J=16.8 Hz, 2H, butane backbone CH$_2$), 1.51-0.92 (br m with major resonances at 1.51, 1.20, 1.02, ester chain CH and CH$_2$), 0.77-0.68, (m with major resonances at 0.75, 0.69, 0.68, ester chain CH$_3$). $^{13}$C NMR (CDCl$_3$, 125 MHz, assigned by DEPT-135): δ 171.83 (minor, overlapped with next peak), 171.73, 171.09 (minor, overlapped with next peak), 170.96 (C=O; not possible to determine if minor peaks are from residual, less-substituted esters or minor tetraester isomers; minor peaks represent 13.1% of total C=O integral), 69.82 and 69.42 (minor), 65.30, 64.94, 64.61, 64.08 (minor), 63.92 (minor), 63.77, 63.58 (minor), 63.42, 63.05, and 62.98 (ester chain OCH$_2$), 46.20-10.32 (ester chain and butane backbone CH, CH$_2$, CH$_3$; butane backbone CH carbon identified at 42.07 (CH) and 33.86 (CH$_2$)). IR (thin film on NaCl): 3454 (w, maybe residual CO$_2$H O—H stretch), 2958 (vs), 2872 (vs). 2720 (w), 1736 (vs, $\nu_{C=O}$), 1464 (s), 1375 (s), 1364 (s), 1333 (m), 1253 (s), 1168 (vs), 1040 (m), 986 (m) cm$^{-1}$. GC/FIMS: m/z 682 (M$^+$, 100; calcd. 682.58). Purity by GC analysis (uncorrected for response factor): 96.2%.

Evaluation Example 1

Differential Scanning Calorimetry (DSC), Viscosity, and Thermogravimetric Analysis (TGA) Property Study of Neat Plasticizers Thermogravimetric Analysis (TGA) was conducted on the neat plasticizers using a TA Instruments AutoTGA 2950HR instrument (25-600° C., 10° C./min, under 60 cc N$_2$/min flow through furnace and 40 cc N$_2$/min flow through balance; sample size 10-20 mg). Table 3 provides a volatility comparison. Differential Scanning Calorimetry (DSC) was also performed on the neat plasticizers, using a TA Instruments 2920 calorimeter fitted with a liquid N$_2$ cooling accessory. Samples were loaded at room temperature and cooled to about −130° C. at 10° C./min and analyzed on heating to 75° C. at a rate of 10° C./min. Table 3 provides a glass transition (T$_g$) comparison. T$_g$s given in Table 3 are midpoints of the second heats (unless only one heat cycle was performed, in which case the first heat T$_g$, which is typically in very close agreement, is given). Comparative data for a common commercial plasticizer (diisononyl phthalate; Jayflex® (DINP), ExxonMobil Chemical Co.) is also included. The glass transition of the C$_5$-OXO butanetetraester plasticizer (Formulation Example 1) was intermediate between those of the purely linear C$_5$ (Comparative Example 2) and purely branched C$_5$ (Comparative Example 1) butanetetraester materials. Typically, linear sidechain ester plasticizers exhibit lower volatilities than branched sidechain ester plasticizers, so that the mixed linear/branched isomer OXO plasticizer would be expected to have intermediate volatility. However, the multi-isomer OXO plasticizer unexpectedly and advantageously had better (lower) volatility than either the pure linear or the pure branched plasticizers.

TABLE 3

Volatility, Viscosity, and Glass Transition Properties of Neat Plasticizers.

| Ex. No. | TGA 1% Wt Loss (° C.) | TGA 5% Wt Loss (° C.) | TGA 10% Wt Loss (° C.) | TGA Wt Loss at 220° C. (%) | DSC T$_g$ (° C.) | Viscosity (20° C., cP) |
|---|---|---|---|---|---|---|
| DINP | 184.6 | 215.2 | 228.5 | 6.4 | −79.1 | 99.2 |
| C.E. 1 | 192.9 | 220.1 | 232.9 | 5.0 | −74.5 | — |
| F.E. 1 | 198.1 | 229.6 | 244.4 | 3.1 | −83.3 | 80.38 |
| C.E. 2 | 196.9 | 225.8 | 239.7 | 3.6 | −86.7 | — |
| C.E. 3 | 243.0 | 288.4 | 304.4 | 0.4 | −71.8 | — |
| C.E. 4 | 180.6 | 222.2 | 238.1 | 4.4 | −82.5 | — |
| F.E. 2 | 220.4 | 254.4 | 269.9 | 1.0 | −80.5 | 119.6 |
| F.E. 3 | 230.9 | 275.7 | 292.2 | 0.8 | −74.9 | 211.4 |

— Data not taken.

Evaluation Example 2

General Procedure for Plasticization of Poly(Vinyl Chloride)

A 5.85 g portion of the plasticizer sample (or comparative commercial plasticizer DINP) was weighed into an Erlenmeyer flask which had previously been rinsed with uninhibited tetrahydrofuran (THF) to remove dust. An 0.82 g portion of a 70:30 by weight solid mixture of powdered Drapex® 6.8 (Crompton Corp.) and Mark® 4716 (Chemtura USA Corp.) stabilizers was added along with a stirbar. The solids were dissolved in 117 mL uninhibited THF. Oxy Vinyls® 240F PVC (11.7 g) was added in powdered form and the contents of the flask were stirred overnight at room temperature until dissolution of the PVC was complete (a PVC solution for preparation of an unplasticized comparative sample was prepared using an identical amount of stabilizer, 100 mL solvent, and 13.5 g PVC). The clear solution was poured evenly into a flat aluminum paint can lid (previously rinsed with inhibitor-free THF to remove dust) of dimensions 7.5" diameter and 0.5" depth. The lid was placed into an oven at 60° C. for 2 hours with a moderate nitrogen purge. The pan was removed from the oven and allowed to cool for a ~5 min period. The resultant clear film was carefully peeled off of the aluminum, flipped over, and placed back evenly into the pan. The pan was then placed in a vacuum oven at 70° C. overnight to remove residual THF. The dry, flexible, typically almost colorless film was carefully peeled away and exhibited no oiliness or inhomogeneity unless otherwise noted. The film was cut into small pieces to be used for preparation of test bars by compression molding (size of pieces was similar to the hole dimensions of the mold plate). The film pieces were stacked into the holes of a multi-hole steel mold plate, pre-heated to 170° C., having hole dimensions 20 mm×12.8 mm×1.8 mm (ASTM D1693-95 dimensions). The mold plate was pressed in a PHI company QL-433-6-M2 model hydraulic press equipped with separate heating and cooling platforms. The upper and lower press plates were covered in Teflon®-coated aluminum foil and the following multistage press procedure was used at 170° C. with no release between stages: (1) 3 minutes with 1-2 ton overpressure; (2) 1 minute at 10 tons; (3) 1 minute at 15 tons; (4) 3 minutes at 30 tons; (5) release and 3 minutes in the cooling stage of the press (7° C.) at 30 tons. A knockout tool was then used to remove the sample bars with minimal flexion. Typically near-colorless, flexible bars were obtained which, when stored at room temperature, showed no oiliness or exudation several weeks after pressing unless otherwise noted.

Evaluation Example 3

Properties of PVC Bars Plasticized with Experimental Plasticizers Versus Commercial Plasticizer DINP Two each of the sample bars prepared in Evaluation Example 2 were visually evaluated for appearance and clarity and further compared to identically prepared bars plasticized with DINP by placing the bars over a standard printed text. The qualitative and relative flexibility of the bars was also crudely evaluated by hand. The various bars were evaluated in different test batches; thus, a new DINP control bar was included with each batch. The bars were placed in aluminum pans which were then placed inside a glass crystallization dish covered with a watch glass. The bars were allowed to sit under ambient conditions at room temperature for at least three weeks and re-evaluated during and/or at the end of this aging period. Table 4 presents appearance rankings and notes.

TABLE 4

Initial and Room Temperature Aging Clarity and Appearance Properties of Plasticized PVC Bars.

| Example No. (Plasticizer Used in Bar) | Initial Clarity Value* | Final Clarity Value (day of evaluation) | Notes on Bar at End of Test |
|---|---|---|---|
| C.E. 1 | 1 | 1 (14) | OK flex/slightly stiff[a] |
| F.E. 1 | 1[b] | 1 (22) | Good flex (sl. > DINP) |
| C.E. 2 | 1[c] | 1 (23) | A little stiff, sl. > DINP |
| C.E. 3 | 2.5[b] | 2.5 (22) | Oily from beginning |
| C.E. 4 | 1 | 1 (35) | Low flex |
| F.E. 2 | 1[b] | 1 (35) | Somewhat stiff, flex < DINP |
| F.E. 3 | 1[b] | 1 (35) | Stiff |
| DINP control for C.E. 1 | 1 | 1 (14) | Moderate/good flex[a] |
| DINP control for F.E. 1, C.E. 3 | 1[b] | 1 (22) | Good flexibility |

TABLE 4-continued

Initial and Room Temperature Aging Clarity and Appearance Properties of Plasticized PVC Bars.

| Example No. (Plasticizer Used in Bar) | Initial Clarity Value* | Final Clarity Value (day of evaluation) | Notes on Bar at End of Test |
|---|---|---|---|
| DINP control for C.E. 2 | 1[c] | 1 (23) | Somewhat stiff |
| DINP control for C.E. 4 | 1 | 1 (35) | Moderate flex |
| DINP control for F.E. 2-3 | 1[b] | 1 (35) | OK flex/slightly stiff |

*1-5 scale, 1 = no distortion, 5 = completely opaque.
— Data not taken.
No bars exhibited oiliness, stickiness, or inhomogeneity unless noted. Bars reflected color, if any, of neat plasticizers.
[a]Evaluated ~1 year after pressing rather than on Day 14.
[b]Evaluated on Day 4.
[c]Day 13.

Evaluation Example 4

98° C. Weight Loss Study of Plasticized PVC Bars

Two each of the PVC sample bars prepared in Evaluation Example 2 were placed separately in aluminum weighing pans and placed inside a convection oven at 98° C. Initial weight measurements of the hot bars and measurements taken at specified time intervals were recorded and results were averaged between the bars. The averaged results are shown in Table 5. Notes on the appearance and flexibility of the bars at the end of the test are also given. The final color of the bars (even DINP control samples) varied between batches; gross comparisons only should be made between bars of different test batches. Similar to what was seen for neat volatility (Evaluation Example 1), the multi-isomer $C_5$-OXO butanetetraester plasticizer (Formulation Example 1) unexpectedly and advantageously had better (lower) volatility than either the pure linear or the pure branched $C_5$ butanetetraester plasticizers (Comparative Examples 1 and 2). Its test bar was slightly better in residual flexibility than its analogous DINP control sample at the conclusion of the test, whereas the pure linear and branched plasticizers (Comparative Examples 1 and 2) showed equivalent residual flexibility to their DINP controls.

TABLE 5

% Weight Loss at 98° C. of Plasticized PVC Bars.

| Example No. (Plast. Used in Bar) | Day 1 | Day 2 | Day 3 | Day 7 | Day 14 | Day 21 | Notes on Bar |
|---|---|---|---|---|---|---|---|
| C.E. 1 | 0.28 | 0.44 | 0.49 | 0.57 | 0.72 | 0.87 | Medium brown, some brittleness |
| F.E. 1 | 0.19 | 0.24 | 0.25 | 0.27 | 0.32 | 0.36 | Light color, flex sl. > DINP |
| C.E. 2 | 0.17 | — | 0.19[b] | 0.25 | 0.34 | 0.41 | Light orange, good flex |
| C.E. 3 | 0.23 | 0.27 | 0.27 | 0.30 | 0.29 | 0.34 | Oily, very dark brown, brittle |
| C.E. 4 | 0.18 | 0.22 | 0.25 | 0.26 | 0.30 | 0.31 | Light orange, moderate flex |
| F.E. 2 | — | — | 0.12 | 0.15 | 0.18 | 0.19 | Med orange, somewhat stiff, flex < DINP |
| F.E. 3 | — | — | 0.11 | 0.15 | 0.17 | 0.17 | Med-dark orange, oily, moderately stiff/stiff |
| DINP Ctrl for C.E. 1 | 0.23 | 0.35 | 0.36 | 0.54 | 0.69 | 1.18[a] | Medium brown, some brittleness |
| DINP Ctrl for F.E. 1, C.E. 3 | 0.21 | 0.22 | 0.24 | 0.37 | 0.56 | 0.60 | Light brown, flexible |
| DINP Ctrl for C.E. 2 | 0.24 | — | 0.22[b] | 0.38 | 0.55 | 0.75 | Light orange, good flex |
| DINP Ctrl for C.E. 4 | 0.20 | 0.27 | 0.31 | 0.36 | 0.48 | 0.56 | Dark med brown, good flex |

TABLE 5-continued

% Weight Loss at 98° C. of Plasticized PVC Bars.

| Example No. (Plast. Used in Bar) | Day 1 | Day 2 | Day 3 | Day 7 | Day 14 | Day 21 | Notes on Bar |
|---|---|---|---|---|---|---|---|
| DINP Ctrl for F.E. 2-3 | — | — | 0.34 | 0.52 | 0.78 | 0.99 | Med-light orange, good flex |

Bars did not exhibit oiliness, stickiness, or inhomogeneity unless noted.
$^a$Data for one bar only; second bar showed weight gain due to weighing error.
$^b$Day 5.

Evaluation Example 5

70° C. Humid Aging Study of Plasticized PVC Bars

Using a standard one-hole office paper hole punch, holes were punched in two each of the sample bars prepared in Evaluation Example 2 about ⅛" from one end of the bar. The bars were hung in a glass pint jar (2 bars per jar) fitted with a copper insert providing a stand and hook. The jar was filled with ~½" of distilled water and the copper insert was adjusted so that the bottom of each bar was ~1" above the water level. The jar was sealed, placed in a 70° C. convection oven, and further sealed by winding Teflon® tape around the edge of the lid. After 21 days the jars were removed from the oven, allowed to cool for ~20 minutes, opened, and the removed bars were allowed to sit under ambient conditions in aluminum pans (with the bars propped at an angle to allow air flow on both faces) or hanging from the copper inserts for ca. 1 week (until reversible humidity-induced opacity had disappeared). The bars were evaluated visually for clarity. All bars exhibited complete opacity during the duration of the test and for several days after removal from the oven. Results are shown in Table 6. Notes on the appearance and flexibility of the bars at the end of the test are also given.

TABLE 6

70° C. Humid Aging Clarity and Appearance Properties of Plasticized PVC Bars.

| Example No. (Plasticizer Used in Bar) | Clarity Value After Test* (days aged at ambient) | Notes on Bar |
|---|---|---|
| C.E. 1 | 1.5 (5) | Good/moderate flex |
| F.E. 1 | 1.5 (8) | Good flex (>DINP) |
| C.E. 2 | 1 (29) | Very good flex |
| C.E. 3 | 4 (8) | Oily, v. brittle, darkest, bubbles in bar |
| C.E. 4 | 1 (14) | Moderate flex |

TABLE 6-continued

70° C. Humid Aging Clarity and Appearance Properties of Plasticized PVC Bars.

| Example No. (Plasticizer Used in Bar) | Clarity Value After Test* (days aged at ambient) | Notes on Bar |
|---|---|---|
| F.E. 2 | 1 (14) | Very oily/sticky, white spots, stiff |
| F.E. 3 | 1-1.5 (14) | Very stiff, very oily |
| DINP control for C.E. 1 | 1.5 (4) | OK flex |
| DINP control for F.E. 1, C.E. 3 | 1 (8) | Somewhat flexible |
| DINP control for C.E. 2 | 1 (29) | OK flex, somewhat stiff |
| DINP control for C.E. 4 | 1 (14) | Moderate flex |
| DINP control for F.E. 2-3 | 1 (14) | Very good flex |

*1-5 scale, 1 = no distortion, 5 = completely opaque.
Bars did not exhibit oiliness, stickiness, or inhomogeneity unless noted. White spots may indicate incomplete reversal of humidity-induced opacity.

Evaluation Example 6

Thermogravimetric Analysis (TGA) Property Study of Plasticized PVC Bars

The sample bars prepared in Evaluation Example 2 were subjected to Thermogravimetric Analysis as described in Evaluation Example 1 to evaluate plasticizer volatility in the formulated test bars. Table 7 provides a volatility comparison. Again, similar to what was seen for neat and 98° C. plasticized volatility (Evaluation Examples 1 and 4), the multi-isomer $C_5$-OXO butanetetraester plasticizer (Formulation Example 1) unexpectedly and advantageously had better (lower) volatility than either the pure linear or the pure branched $C_5$ butanetetraester plasticizers (Comparative Examples 1 and 2).

TABLE 7

Volatility Properties of Plasticizers in Plasticized PVC Bars (and Films$^a$).

| Example No. (Plasticizer Used in Bar) | TGA 1% Wt Loss (° C.) | TGA 5% Wt Loss (° C.) | TGA 10% Wt Loss (° C.) | TGA Wt Loss at 220° C. (%) | Age of Bar at Test (Days) |
|---|---|---|---|---|---|
| Neat PVC | 129.9 | 192.3 | 255.4 | 6.3 | 23 |
| DINP | 204.6 | 247.4 | 257.6 | 1.8 | 58 |
| C.E. 1 | 206.5 | 242.2 | 253.7 | 1.7 | 46 |
| F.E. 1 | 214.6 | 245.6 | 255.2 | 1.3 | 277 |
|  | *(223.6)* | *(248.6)* | *(259.1)* | *(0.84)* | *(241)* |

TABLE 7-continued

Volatility Properties of Plasticizers in Plasticized PVC Bars (and Films[a]).

| Example No.<br>(Plasticizer Used<br>in Bar) | TGA 1% Wt<br>Loss (° C.) | TGA 5% Wt<br>Loss (° C.) | TGA 10% Wt<br>Loss (° C.) | TGA Wt Loss<br>at 220° C. (%) | Age of Bar at<br>Test (Days) |
|---|---|---|---|---|---|
| C.E. 2 | 210.2 | 247.5 | 256.8 | 1.4 | 64 |
|  | *(204.7)* | *(243.8)* | *(254.9)* | *(1.7)* | *(29)* |
| C.E. 3 | — | — | — | — | — |
| C.E. 4 | 211.6 | 245.7 | 255.3 | 1.4 | 254 |
|  | *(221.4)* | *(247.6)* | *(258.6)* | *(0.93)* | *(218)* |
| F.E. 2 | — | — | — | — | — |
| F.E. 3 | — | — | — | — | — |

— Data not taken.
[a]Data for films where available is shown in italics in parentheses below the bar data.

Evaluation Example 7

Demonstration of PVC Plasticization of PVC via Differential Scanning Calorimetry (DSC)

Differential Scanning Calorimetry (DSC) was performed on the compression-molded sample bars, or optionally, small quantities of the precursor cast films, prepared in Evaluation Example 2 using a TA Instruments 2920 calorimeter fitted with a liquid $N_2$ cooling accessory. Samples were loaded at room temperature and cooled to −90° C. at 10° C./min, and then analyzed on heating at a rate of 10° C./min to 150-170° C. for plasticized PVC bars, and to 100° C. for the comparative neat PVC bar. For the runs conducted using molded bars, small portions of the sample bars (typical sample mass 5-7 mg) were cut for analysis, making only vertical cuts perpendicular to the largest surface of the bar to preserve the upper and lower compression molding "skins"; the pieces were then placed in the DSC pans so that the upper and lower "skin" surfaces contacted the bottom and top of the pan. Table 8 provides the first heat $T_g$ onset, midpoint, and end for neat PVC and the plasticized bars. A lowering and broadening of the glass transition for neat PVC was observed upon addition of the experimental plasticizers, indicating plasticization and extension of the flexible temperature range of use for neat PVC (for aid in calculating the numerical values of these broad transitions, the DSC curve for each plasticized bar was overlaid with the analogous Dynamic Mechanical Thermal Analysis (DMTA) curve, taken and analyzed as described in Evaluation Example 8 below, since the DMTA curve provides additional guidance about the proper temperature regions for the onset, midpoint, and end of $T_g$). The $T_g$ onset, midpoint, and end for the purely linear $C_5$ butanetetraester plasticizer (Comparative Example 2) were much lower (indicating superior plasticization) as compared to those for the purely branched $C_5$ butanetetraester plasticizer (Comparative Example 1). Unexpectedly, the onset, midpoint, and end for the multi-isomer $C_5$-OXO butanetetraester plasticizer (Formulation Example 1) were not a weighted average of those for the purely linear and purely branched materials, but were almost equivalent to those for the purely linear material. Thus, the multi-isomer $C_5$-OXO butanetetraester plasticizer unexpectedly and advantageously provided lower volatility than, but equivalent DSC-quantified plasticization to, the analogous purely linear $C_5$ butanetetraester plasticizer (i.e., better property balance). FIG. 1 shows a DSC $T_g$ comparison between neat PVC, the neat $C_5$-OXO butanetetraester plasticizer (Formulation Example 1), and the PVC bar plasticized with the $C_5$-OXO butanetetraester plasticizer.

TABLE 8

Glass Transition Onset, Midpoint, and End for Plasticized PVC Bars (and Films[a])

| Example No.<br>(Plasticizer Used<br>in Bar) | $T_g$ Onset<br>(° C.) | $T_g$ Midpt<br>(° C.) | $T_g$ End<br>(° C.) | $T_m$ Max (° C.) and<br>$\Delta H_f$ (J/g)[b] | Age of Bar<br>at Test<br>(Days) |
|---|---|---|---|---|---|
| Neat PVC | 44.5 | 46.4 | 48.9 | not anal. | 42 |
| DINP | −37.8 | −24.8 | −12.2 | not anal. (v. small) | 53 |
| C.E. 1 | −21.9 | −8.6 | 4.8 | not anal. (v. small) | 50 |
| F.E. 1 | −37.0 | −20.6 | −4.0 | 56.8 (0.88) | 240 |
|  | *(−42.2)* | *(−27.0)* | *(−11.5)* | *(62.7 (1.5))* |  |
| C.E. 2 | −38.1 | −21.0 | −3.8 | 53.0 (0.56) | 28 |
|  | *(−40.1)* | *(−26.3)* | *(−12.9)* | *(58.0 (1.3))* |  |
| C.E. 3 | — | — | — | — | — |
| C.E. 4 | −19.2 | −4.4 | 10.3 | 61.4 (1.1) | 217 |
|  | *(−18.5)* | *(−5.8)* | *(6.8)* | *(not anal.)* |  |
| F.E. 2 | — | — | — | — | — |
| F.E. 3 | — | — | — | — | — |

— Data not obtained.
[a]Data for films where available is shown in italics in parentheses below the bar data.
[b]Some sample bars showed a weak melting point ($T_m$) from the crystalline portion of PVC. Often this weak transition was not specifically analyzed, but data is given here in instances where it was recorded.

Evaluation Example 8

Demonstration of Plasticization of PVC with Mixed Tetraesters via Dynamic Mechanical Thermal Analysis (DMTA)

Three-point bend Dynamic Mechanical Thermal Analysis (DMTA) with a TA Instruments DMA Q980 fitted with a liquid $N_2$ cooling accessory and a three-point bend clamp assembly was used to measure the thermo-mechanical performance of neat PVC and the PVC/plasticizer blend sample bars prepared in Evaluation Example 2. Samples were loaded at room temperature and cooled to −60° C. at a cooling rate of 3° C./min. After equilibration, a dynamic experiment was performed at one frequency using the following conditions: 3° C./min heating rate, 1 Hz frequency, 20 micrometer amplitude, 0.01 pre-load force, force track 120%. Two or three bars of each sample were typically analyzed; numerical data was taken from the bar typically exhibiting the highest room temperature storage modulus (the bar assumed to have the fewest defects) unless another run was preferred for data quality. Glass transition onset values were obtained by extrapolation of the tan delta curve from the first deviation from linearity. The DMTA measurement gives storage modulus (elastic response modulus) and loss modulus (viscous response modulus); the ratio of loss to storage moduli at a given temperature is tan delta. The beginning (onset) of the $T_g$ (temperature of brittle-ductile transition) was obtained for each sample by extrapolating a tangent from the steep inflection of the tan delta curve and the first deviation of linearity from the baseline prior to the beginning of the peak.

Table 9 provides a number of DMTA parameters for neat PVC and PVC bars plasticized with the tetraesters prepared in the Comparative and Formulation Examples: $T_g$ onset (taken from tan delta); peak of the tan delta curve; storage modulus at 25° C.; and the temperature at which the storage modulus equals 100 MPa (this temperature was chosen to provide an arbitrary measure of the temperature at which the PVC loses a set amount of rigidity; too much loss of rigidity may lead to processing complications for the PVC material). The flexible use temperature range of the plasticized PVC samples was evaluated as the range between the $T_g$ onset and the temperature at which the storage modulus was 100 MPa. A lowering and broadening of the glass transition for neat PVC was observed upon addition of the plasticizers, indicating plasticization and extension of the flexible temperature range of use for neat PVC. Plasticization (enhanced flexibility) was also demonstrated by lowering of the PVC room temperature storage modulus.

Figure 2:
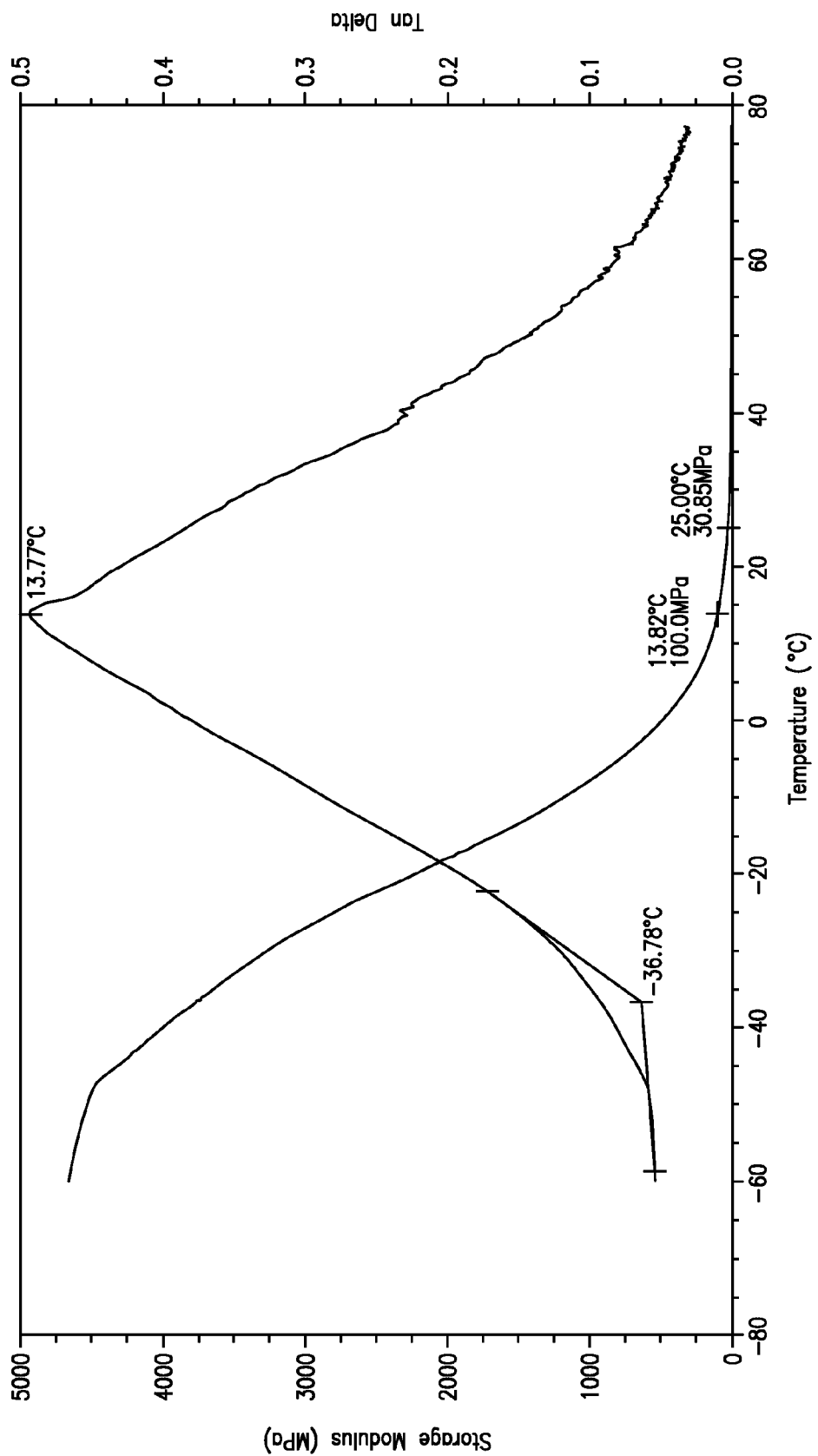
FIG. 2 shows a DMTA (dymanic mechanical thermal analysis) overlay of storage modulus versus tan delta curve for PVC plasticized with the OXO $C_5$ butanetetraester plasticizer of Formulation Example 1.

In these experiments, the most robustly measured plasticization parameters (tan delta peak, 25° C. storage modulus) for the multi-isomer $C_5$-OXO butanetetraester plasticizer (Formulation Example 1) were intermediate between those for the purely linear and purely branched $C_5$ butanetetraester plasticizers (Comparative Examples 1 and 2). However, the multi-isomer $C_5$-OXO butanetetraester plasticizer unexpectedly exhibited an equivalently low temperature of 100 MPa storage modulus to the purely linear $C_5$ butanetetraester plasticizer (in combination with unexpectedly and advantageously lower volatility). FIG. 2 shows a DMTA overlay of storage modulus versus tan delta curve for PVC plasticized with the $C_5$-OXO butanetetraester plasticizer of Formulation Example 1.

TABLE 9

Various DMTA Thermal Parameters for Plasticized PVC Bars

| Example No. (Plast. Used in Bar) | Tan Δ $T_g$ Onset (° C.) | Tan Δ Peak (° C.) | 25° C. Storage Mod. (MPa) | Temp. of 100 MPa Storage Mod. (° C.) | Flexible Use Range (° C.)[a] | Age of Bar at Test (Days) |
|---|---|---|---|---|---|---|
| Neat PVC | 44.0 | 61.1 | 1433 | 57.1 | 13.1 | 28 |
| DINP | −37.6 | 17.1 | 48.6 | 16.9 | 54.5 | 55 |
| C.E. 1 | −38.1 | 21.5 | 66.1 | 21.1 | 59.2 | 36 |
| F.E. 1 | −36.8 | 13.8 | 30.9 | 13.8 | 50.6 | 240 |
| C.E. 2 | −40.7 | 5.7 | 23.6 | 13.8 | 54.5 | 48 |
| C.E. 3 | — | — | — | — | — | — |
| C.E. 4 | −17.8 | 26.9 | 67.2 | 23.2 | 41.0 | 237 |
| F.E. 2 | — | — | — | — | — | — |
| F.E. 3 | — | — | — | — | — | — |

— Data not obtained.
[a]Difference between temperature of 100 MPa storage modulus and onset of $T_g$.

The meanings of terms used herein shall take their ordinary meaning in the art; reference shall be taken, in particular, to Handbook of Petroleum Refining Processes, Third Edition, Robert A. Meyers, Editor, McGraw-Hill (2004). In addition, all patents and patent applications, test procedures (such as ASTM methods), and other documents cited herein are fully incorporated by reference to the extent such disclosure is not inconsistent with this disclosure and for all jurisdictions in which such incorporation is permitted. Also, when numerical lower limits and numerical upper limits are listed herein, ranges from any lower limit to any upper limit are contemplated. Note further that Trade Names used herein are indicated by a ™ symbol or ® symbol, indicating that the names may be protected by certain trademark rights, e.g., they may be registered trademarks in various jurisdictions.

The disclosure has been described above with reference to numerous embodiments and specific examples. Many variations will suggest themselves to those skilled in this art in light of the above detailed description. All such obvious variations are within the full intended scope of the appended claims.

What is claimed is:

1. Tetraesters of an aliphatic tetracarboxylic acid and OXO-alcohols, wherein the ester moieties are mixed-isomer alkyl residues of $C_5$ Oxo-alcohols, and wherein the alkyl residues have from 0.3 to 0.4 beta branches per residue, and wherein the tetracarboxylic acid is 1,2,3,4-butanetetracarboxylic acid.

2. The tetraesters of claim 1, wherein the alkyl residues comprise a mixture of linear and branched alkyl groups.

3. The tetraesters of claim 1, wherein the alkyl residues have from 0.2 to 3.0 total branches per residue.

4. A plasticizer compound of the formula:

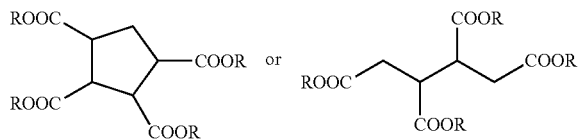

wherein each R is the alkyl residue of $C_5$ OXO-alcohols, wherein collectively R represents mixed-isomer alkyl residues of $C_5$ OXO-alcohols and wherein the alkyl residues have from 0.3 to 0.4 beta branches per residue.

5. The plasticizer compound of claim 4, wherein the alkyl residues comprise a mixture of linear and branched alkyl groups.

6. The plasticizer compound of claim 4, wherein the alkyl residues have from 0.2 to 3.0 total branches per residue.

7. A plasticizer compound of the formula:

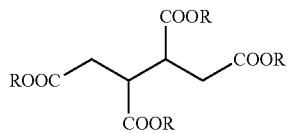

wherein each R is the alkyl residue of $C_5$ OXO-alcohols, and wherein the alkyl residues have from 0.3 to 0.4 beta branches per residue.

8. The plasticizer compound of claim 7, wherein the alkyl residues comprise a mixture of linear and branched alkyl groups.

9. The plasticizer compound of claim 7, wherein the alkyl residues have from 0.2 to 3.0 total branches per residue.

10. A composition comprising a polymer and a plasticizer of the formula:

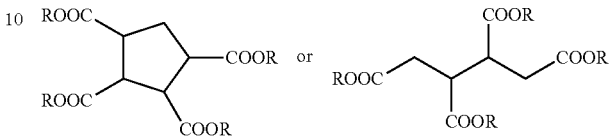

wherein each R is the alkyl residue of $C_5$ OXO-alcohols, wherein collectively R represents mixed-isomer alkyl residues of $C_5$ OXO-alcohols and wherein the alkyl residues have from 0.3 to 0.4 beta branches per residue.

11. The composition of claim 10, wherein the alkyl residues comprise a mixture of linear and branched alkyl groups.

12. The composition of claim 10, wherein the alkyl residues have from 0.2 to 3.0 total branches per residue.

13. The composition of claim 10, wherein the polymer is selected from the group consisting of vinyl chloride resins, polyesters, polyurethanes, ethylene-vinyl acetate copolymer, rubbers, poly(meth)acrylics and combinations thereof.

14. The composition of claim 13, wherein the polymer is polyvinylchloride.

* * * * *